United States Patent
Hoos et al.

(10) Patent No.: US 7,829,058 B2
(45) Date of Patent: Nov. 9, 2010

(54) PROCESS FOR THE PURIFICATION OF (HYDRO) HALOCARBONS

(75) Inventors: Paul Andrew Hoos, Cheshire (GB); Stuart Corr, Cheshire (GB)

(73) Assignee: Ineos Fluor Holdings Limited (GB)

( * ) Notice: Subject to any disclaimer, the term of this patent is extended or adjusted under 35 U.S.C. 154(b) by 989 days.

(21) Appl. No.: 10/546,336

(22) PCT Filed: Feb. 19, 2004

(86) PCT No.: PCT/GB2004/000659

§ 371 (c)(1), (2), (4) Date: Jun. 27, 2006

(87) PCT Pub. No.: WO2004/074225

PCT Pub. Date: Sep. 2, 2004

(65) Prior Publication Data

US 2007/0015944 A1    Jan. 18, 2007

(30) Foreign Application Priority Data

Feb. 20, 2003 (GB) ................ 0303972.4

(51) Int. Cl.
  *C07C 17/389* (2006.01)
  *C07C 19/08* (2006.01)
  *B01J 29/00* (2006.01)
(52) U.S. Cl. .................. 423/490; 585/820
(58) Field of Classification Search .......... None
  See application file for complete search history.

(56) References Cited

U.S. PATENT DOCUMENTS

| 4,849,558 | A | | 7/1989 | Goodman |
| 4,906,796 | A | | 3/1990 | Yates |
| 4,957,715 | A | * | 9/1990 | Grover et al. ............ 423/228 |
| 5,288,930 | A | | 2/1994 | Shields et al. |
| 6,074,459 | A | * | 6/2000 | Gingrich et al. ............ 95/118 |
| 6,274,782 | B1 | | 8/2001 | Ohno et al. |
| 6,527,917 | B1 | * | 3/2003 | Kohno et al. ............ 203/67 |

FOREIGN PATENT DOCUMENTS

| WO | WO 94/01386 | | 1/1994 |
| WO | PCT/JP98/03590 | * | 3/1999 |
| WO | WO 01/83412 A2 | | 11/2001 |
| WO | WO 01/83412 A3 | | 11/2001 |

OTHER PUBLICATIONS www.alibaba.com/product-gs/202552066/ZSM_ZSM_5 molecular sieve.html ZSM, ZSM-5 mlecular sieve features, specifications.*
www.alibaba.com/product-gs/202552066/ZSM_ZSM_5 molecular sieve.html ZSM, ZSM-5 mlecular sieve features, specification (Jul. 31, 2008).*
International Search Report re application No. PCT/GB04/000659, Jun. 25, 2004, Ineos Fluor Holdings Ltd.
Written Opinion re application No. PCT/GB04/000659, Jun. 25, 2004, Ineos Fluor Holdings Ltd.
International Preliminary Report on Patentability re application No. PCT/GB04/000659, Jun. 7, 2005, Ineos Fluor Holdings Ltd.
Office Action in corresponding Japanese Application No. 2006-502297.

* cited by examiner

*Primary Examiner*—Daniel M Sullivan
*Assistant Examiner*—Yevegeny Valenrod
(74) *Attorney, Agent, or Firm*—Cook Alex Ltd.

(57) ABSTRACT

A process for treating a composition comprising one or more desired (hydro)halocarbons and one or more undesired sulphur containing impurities so as to reduce the concentration of at least one undesired sulphur containing impurity, the process comprising contacting the composition with an adsorbent comprising an acid stable molecular sieve having a pore size of from 2 to 10 Å and/or an activated carbon.

27 Claims, 5 Drawing Sheets

PROCESS FOR THE PURIFICATION OF (HYDRO) HALOCARBONS

CROSS REFERENCE TO RELATED APPLICATIONS

This application is a national stage application based upon International Application No. PCT/GB2004/000659, filed Feb. 19, 2004, which claims priority from Great Britain Application No. GB 0303972.4, filed Feb. 20, 2003.

BACKGROUND AND SUMMARY OF THE INVENTION

This invention relates to a process for reducing the concentration of undesired sulphur containing impurities and, preferably, of undesired halogenated organic compounds in (hydro)halocarbon compositions.

(Hydro)halocarbons typically have a slight ethereal odour. Contamination by sulphur containing impurities can cause a momentary or even a lingering malodour.

Malodour can be caused both by inorganic and organic sulphur containing compounds, such as hydrogen sulphide, carbon disulphide, carbonyl sulphide, sulphur dioxide, sulphur trioxide, sulphuric acid, dimethyldisulphide, ethanethiol and diethyldisulphide.

Sulphur containing impurities may be introduced to (hydro)halocarbons during manufacture, for example from contaminants in hydrofluoric acid. Hydrofluoric acid may contain sulphur containing contaminants such as sulphur dioxide, sulphur trioxide, hydrogen sulphide and sulphuric acid, which may react with (hydro)halocarbons and/or their precursors during production to form sulphur containing impurities such as dimethyldisulphide, ethanethiol and diethyldisulphide. Some of these impurities survive known separation processes and reside in the bulk material.

Malodour can be unpleasant in any use of (hydro)halocarbons, particularly in dispensive uses and most particularly in pharmaceutical products where the (hydro)halocarbon is taken into the body.

It is, therefore, desirable to remove sulphur containing impurities from (hydro)halocarbons, such as halogenated alkanes, alkenes and ethers. Such removal is particularly important for pharmaceutical grade products, such as those used as propellants in pressurised metered dose inhalers.

Purification techniques that are well known in the art, such as distillation, are typically unsuitable for removing sulphur containing impurities from (hydro)halocarbons. Distillation does not achieve the very high purities required to provide (hydro)halocarbons without malodour.

Known processes, therefore, typically do not remove all of the malodour causing sulphur containing impurities.

Techniques used in the art to remove halogenated organic impurities from halogenated alkanes include the use of molecular sieves. Examples of the use of molecular sieves to remove such impurities are described in U.S. Pat. No. 6,274,782, U.S. Pat. No. 4,906,796 and U.S. Pat. No. 5,288,930.

U.S. Pat. No. 6,274,782 describes the separation of 1,1-difluoroethane (R-152a) from hexafluoroethane (R-116) using a combination of molecular sieves 5A, 10X and 13X.

U.S. Pat. No. 4,906,796 describes the purification of 1,1,1,2-tetrafluoroethane (R-134a) using carbon molecular sieves and zeolites. The process described removes chlorodifluoroethene (R-1122) from R-134a.

U.S. Pat. No. 5,288,930 describes the removal of chlorodifluoroethene (R-1122) from 1,1,1,2-tetrafluoroethane (R-134a) using a zeolite having a pore size of from 3.5 to 4.8 Å with potassium as the counter ion.

The listing or discussion of a prior-published document in this specification should not necessarily be taken as an acknowledgement that the document is part of the state of the art or is common general knowledge.

The molecular sieves previously used to remove halogenated organic impurities from halogenated alkanes typically do not also remove sulphur containing impurities to the extent necessary to remove malodour.

There is, therefore, a need for a process that effectively and efficiently reduces the concentration of sulphur containing impurities or removed these impurities from (hydro)halocarbons.

The present invention provides a new process for reducing the concentration of at least one undesired sulphur containing impurity and, preferably, of at least one undesired halogenated hydrocarbon from a (hydro)halocarbon composition.

DESCRIPTION OF THE PREFERRED EMBODIMENTS

Figure 1:
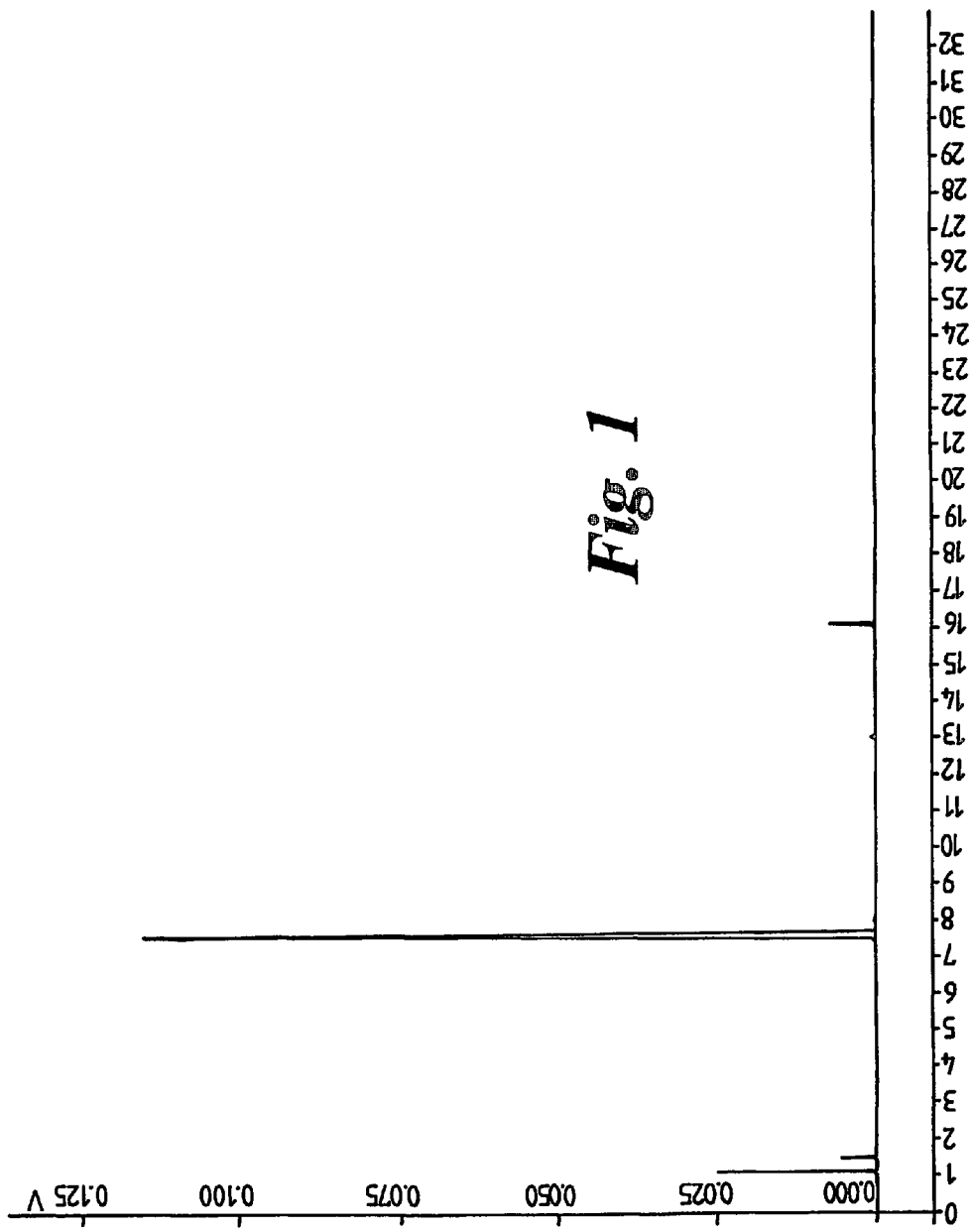
FIGS. 1-5 are gas chromatograms of (hydro) halocarbons during various stages of processing in accordance with the present invention.

According to a first aspect of the invention, there is provided a process for treating a composition comprising one or more desired (hydro)halocarbons and one or more undesired sulphur containing impurities so as to reduce the concentration of at least one undesired sulphur containing impurity, the process comprising contacting the composition with an adsorbent comprising an acid stable molecular sieve having a pore size of from 2 to 10 Å and/or an activated carbon.

If the composition to be treated also comprises one or more undesired halogenated organic compounds, the process may also reduce the concentration of at least one undesired halogenated organic compound.

The process typically removes at least 50% by weight, more preferably at least 90% by weight and even more preferably at least 98% by weight of the sulphur containing impurities. Preferably, the process reduces the concentration of sulphur containing impurities to levels below the limit of detection by smell and/or by gas chromatography with pulsed flame photometric detection set to "sulphur" mode. Thus, the process typically is effective at removing malodour caused by sulphur containing impurities.

The process does not necessarily reduce the concentration of every one of the one or more undesired sulphur containing impurities, but it may do so. Similarly, when the composition to be treated comprises one or more undesired halogenated organic compounds, it does not necessarily reduce the concentration of every one of these compounds, but it may do so.

The process typically can be used to treat any (hydro) halocarbon that is made by any method. It is particularly suitable for treating any (hydro)halocarbon that is made using hydrofluoric acid. As discussed above, hydrofluoric acid often contains sulphur containing impurities that may be transferred into the (hydro)halocarbon product or may react to form further sulphur containing compounds.

By the term "(hydro)halocarbon" we mean a compound that contains carbon, one or more halogen atoms and, optionally, hydrogen and/or oxygen. The (hydro)halocarbon may be saturated or unsaturated. Preferably, the (hydro)halocarbon has a carbon chain length of from one to four.

The composition to be treated may comprise one or more desired (hydro)halocarbons selected from halogenated alkanes, halogenated alkenes and halogenated ethers.

Preferably, the composition to be treated comprises at least one desired (hydro)halocarbon selected from hydrofluoroalkanes, hydrochlorofluoroalkanes, chlorofluoroalkanes, perfluoroalkanes, perchloroalkenes, hydrochloroalkenes and (hydro)fluoroethers. The process of the invention is particularly suitable for treating compositions in which the or each desired (hydro)halocarbon contains fluorine atoms as the only halogen atoms, for example hydrofluoroalkanes, perfluoroalkanes and/or (hydro)fluoroethers. It is particularly preferred that the or each desired compound is a hydrofluoroalkane.

By the term "hydrofluoroalkane", we mean an alkane which contains only carbon, hydrogen and fluorine atoms.

By the term "hydrochlorofluoroalkane", we mean an alkane which contains only carbon, chlorine, fluorine and hydrogen atoms.

By the term "chlorofluoroalkane", we mean an alkane which contains only carbon, chlorine and fluorine atoms.

By the term "perfluoroalkane", we mean an alkane which contains only carbon and fluorine atoms.

By the term "perchloroalkene", we mean an alkene which contains only carbon and chlorine atoms.

By the term "hydrochloroalkene", we mean an alkene which contains only carbon, hydrogen and chlorine atoms.

By the term "(hydro)fluoroether", we mean an ether which contains carbon, fluorine and oxygen atoms and, optionally, hydrogen atoms.

Desired hydrofluoroalkanes that may be purified include 1,1,1,2-tetrafluoroethane (R-134a), 1,1,1,2,3,3,3-heptafluoropropane (R-227ea), 1,1-difluoroethane (R-152a), 1,1,1-trifluoroethane (R-143a), pentafluoroethane (R-125), difluoromethane (R-32), 1,1,1,3,3-pentafluoropropane (R-245fa), 1,1,2,2,3-pentafluoropropane (R-245ca), 1,1,1,3,3-pentafluorobutane (R-365mfc) and hexafluorobutane (R-356). The use of the process of the present invention to purify 1,1,1,2-tetrafluoroethane (R-134a) and/or 1,1,1,2,3,3,3-heptafluoropropane (R-227ea) is particularly preferred.

Desired hydrochlorofluoroalkanes that may be purified include chlorodifluoromethane (R-22), 1,1-dichloro-1-fluoroethane (R-141b), 1-chloro-1,1-difluoroethane (R-142b), 1,1,1-trifluoro-2-chloroethane (R-133a), 2,2-dichloro-1,1,1-trifluoroethane (R-123), 2-chloro-1,1,1,2-tetrafluoroethane (R-124) and dichloropentafluoropropane (R-225, all isomers).

Desired chlorofluoroalkanes that may be purified include dichlorodifluoromethane (R-12), 1,2-dichloro-1,1,2,2-tetrafluoroethane (R-114) and 1,1,1-trichloro-2,2,2-trifluoroethane (R-113a).

Desired perfluoroalkanes that may be purified include perfluoromethane (R-14), perfluoroethane (R-116), perfluoropropane (R-218), perfluorobutane, perfluorocyclobutane, perfluoropentane and perfluorohexane.

A desired perchloroalkene that may be purified is perchloroethene.

Desired hydrochloroalkenes that may be purified include trichloroethene and vinyl chloride.

Desired hydrofluoroethers that may be purified include 1,1,1,3,3,3-hexafluoroisopropyl fluoromethyl ether (Sevoflurane/$(CF_3)_2CHOCH_2F$), 1,1,1-trifluoro-2-chloroethyl difluoromethyl ether (Isoflurane/$CF_3CHClOCF_2H$), 1,1,1,2-tetrafluoroethyl difluoromethyl ether (Desflurane/$CF_3CHFOCF_2H$), trifluoromethyl difluoromethyl ether (E-125/$CF_3OCF_2H$) and 1,1,1-trifluoroethyl tetrafluoroethyl ether (HFE-347pcf/$CF_3CH_2OCF_2CF_2H$).

The process can reduce the concentration of inorganic and/or organic sulphur containing impurities. It is particularly advantageous to use the process to reduce the concentration of organic sulphur containing impurities because these are typically more difficult to remove using standard techniques known to those skilled in the art.

By the term "organic sulphur containing impurities", we mean compounds containing at least carbon and sulphur, optionally including other atoms such as hydrogen and oxygen. Organic sulphur containing impurities that can be removed/reduced include (but are not limited to) dimethyldisulphide, ethanethiol, diethyldisulphide, carbon disulphide and carbonyl sulphide.

By the term "inorganic sulphur containing impurities", we mean compounds containing at least sulphur, optionally including other atoms such as hydrogen and oxygen. Inorganic sulphur containing impurities that can be removed/reduced include (but are not limited to) hydrogen sulphide, sulphur dioxide, sulphur trioxide and/or sulphuric acid.

Before treatment, sulphur containing impurities typically are present in (hydro)halocarbons compositions at levels of from the limit of detection to about 0.1% by volume. For example, dimethyldisulphide may be present at levels of 40 ppb and above, and/or ethanethiol at levels of from 5 to 10 ppb and/or diethyldisulphide at levels of from 5 to 10 ppb.

The process typically reduces the concentration of the sulphur containing impurities to levels below the limit of detection by standard equipment, i.e. so that they are virtually entirely removed. By the term "limit of detection", we mean the point at which the sulphur containing impurities cannot be detected by smell and/or by gas chromatography with pulsed flame photometric detection set to "sulphur" mode. For example, the limit of detection by gas chromatography may be at levels of approximately 5 ppb and below.

The process of the present invention can be used to remove or reduce the concentration of one or more undesired halogenated organic compounds. The process is particularly suitable for the removal/reduction of halogenated organic compounds containing one or two carbon atoms, although other undesired halogenated organic compounds may also be removed. When the undesired halogenated organic compounds contain two or more carbon atoms, they may be saturated or unsaturated.

By the term "undesired halogenated organic compounds" we mean undesired compounds that contain carbon, one or more halogen atoms and, optionally, hydrogen. The undesired halogenated organic compounds preferably contain fluorine and/or chlorine and/or bromine, more preferably fluorine and/or chlorine.

Halogenated organic compounds that may be removed/reduced using the process of the present invention include (but are not limited to) chlorofluoromethanes, e.g chlorodifluoromethane (R-22) and chlorofluoromethane (R-31), difluoroethanes, e.g. 1,2-difluoroethane (R-152) and 1,1-difluoroethane (R-152a), tetrafluoroethanes, e.g. 1,1,1,2-tetrafluoroethane (R-134a) and 1,1,2,2-tetrafluoroethane (R-134), chlorodifluoroethenes, e.g. chlorodifluoroethene (R-1122), cis-chlorodifluoroethene (R-1122a) and trans-chlorodifluoroethene (R-1122a), chlorofluoroethenes, e.g. chlorofluoroethene (R-1131a), cis-chlorofluoroethene (R-1131) and trans-chlorofluoroethene (R-1131).

The process uses an adsorbent comprising an acid stable molecular sieve having a pore size of from 2 to 10 Å and/or an activated carbon.

The pore size of the acid stable molecular sieve is preferably from 3 to 5 Å, more preferably from 3 to 4 Å.

By the term "acid stable molecular sieve", we mean a molecular sieve that does not substantially decompose when it is treated with aqueous acid of a pH of about 3.

Suitable acid stable molecular sieves include acid washed molecular sieves. By the term "acid washed molecular sieve", we mean a molecular sieve that is washed with an acid during its preparation. This acid washing removes a proportion of the basic sites from the molecular sieve, which affects the absorption properties of the molecular sieve and reduces/prevents reaction with acid on contact therewith. For example, suitable acid stable molecular sieves are acid stable zeolites that may be obtained by washing a conventional zeolite with an aqueous solution of an acid such as hydrochloric acid.

Alternatively, acid stable molecular sieves such as acid stable zeolites may be specifically synthesised using methods well known in the art.

Acid stable zeolites tend to have a higher Si:Al ratio than conventional zeolites having a similar pore diameter. Acid stable zeolites suitable for use in the present invention include, but are not limited to, those having a $SiO_2:Al_2O_3$ ratio of 2:1 or higher. For example, a chabazite having a $SiO_2:Al_2O_3$ ratio of 2:1 or higher may be used.

The skilled person would be able to determine whether a molecular sieve is acid stable using his common general knowledge. This could be done by testing whether the molecular sieve significantly decomposes in acid.

The acid stable molecular sieve may be a zeolite and/or a molecular sieve carbon. Preferably, the acid stable molecular sieve comprises a zeolite, for example an acid washed zeolite.

Zeolite molecular sieves have the formula $M_x[(Al_2O_3)_x(SiO_2)_y].zH_2O$, where M is one or more of sodium, potassium, calcium and magnesium. This generic formula is an industry standard and the nature of M and the values of x, y and z vary according to the particular manufacturer.

A zeolite molecular sieve that is suitable for use in the process is AW-300, which is a molecular sieve that would be well known to a person skilled in the art.

An example of a zeolite molecular sieve that is suitable for use in the process is MOLSIV™ AW-300, which can be obtained from UOP Limited (USA). MOLSIV™ AW-300 is a pelleted molecular sieve. It is a clay bound, acid resistant synthetic molecular sieve product that adsorbs molecules with critical diameters of up to 4 Å.

Another AW-300 molecular sieve suitable for use in the process can be obtained from Sigma-Aldrich (USA).

Another zeolite molecular sieve that is suitable for use in the process is AW-500, which is a molecular sieve that would be well known to a person skilled in the art.

Activated carbon adsorbents would be well known to a person skilled in the art.

Suitable activated carbon adsorbents include those having a micro-porous structure in which greater than 60% of the pore size distribution proportion falls within the 2 to 20 Å range. Such activated carbon adsorbents may be derived from coconut husk. An example of such an activated carbon adsorbent is grade 207C activated carbon, which can be obtained from Sutcliffe Speakman Carbons Limited (UK).

The adsorbent may be used in the form of a powder, pellets and/or sintered products, which may, for example be in combination with silica gel. It is preferred to use the adsorbent in the form of pellets, as these are easy to handle on an industrial scale. Suitable pellets include those in which a zeolite is bound with clay.

The present inventors have found that adsorbents comprising an acid stable molecular sieve having a pore size of from 2 to 10 Å and/or an activated carbon are highly effective at removing sulphur containing impurities from (hydro)halocarbons such as 1,1,1,2-tetrafluoroethane (R-134a), 1,1,1,2,3,3,3-heptafluoropropane (R-227ea), 1,1,1,3,3-pentafluoropropane (R-245fa) and 1,1,2,2,3-pentafluoropropane (R-245ca). The adsorbents used in the present invention are more effective at removing sulphur containing impurities compared to other known molecular sieves, such as 4A, 5A and 13X. The molecular sieves 4A, 5A and 13X would be well known to a person skilled in the art.

If required, the adsorbent may be dried before use. Alternatively, the adsorbent may be used in the form it is obtained from the manufacturer. The preferred moisture level is less than about 1.5% by weight.

The process may be conducted in either the liquid or the vapour phase, but the liquid phase is preferred as it is more economical to run.

Of course, the process should be conducted at a temperature that allows absorption to occur. This temperature is typically less than about 200° C., preferably less than about 150° C., more preferably less than about 100° C. and even more preferably about 60° C. For example, the process may be conducted at ambient temperature or temperatures below ambient temperature. The skilled person would readily be able to determine a suitable temperature taking into consideration factors such as the nature of the desired compounds.

The process of the present invention may be conducted at any pressure sufficient to keep the components of the composition in the liquid or vapour phase, as appropriate. If the process is conducted in the liquid phase, it is preferably conducted at its autogeneous pressure, i.e. the pressure that the liquid itself exerts, or higher if desired. If the process is conducted in the vapour phase, it is preferably conducted at a pressure of from 0.1 MPa to the saturation pressure. For a given temperature, the saturation pressure of a pure component is that pressure at which vaporisation of the liquid takes place.

Typically, the process is conducted by circulating the composition to be treated through a polishing bed containing the adsorbent. The polishing bed may be a packed or fluidised bed, although a packed bed is preferred.

The contact time depends on the amount of adsorbent being used and on its freshness. The skilled person would readily be able to determine a suitable contact time for a particular process.

The effectiveness of the adsorbent used in the process will deteriorate with time. The time that it takes for the adsorbent to deteriorate depends on a number of factors, such as the ratio of the amount of adsorbent to the amount of the composition being treated.

The process of the present invention may further comprise the step of regenerating the adsorbent after it has been contacted with the (hydro)halocarbon composition. For example, the adsorbent may be regenerated by contacting it with a heated nitrogen stream or by heating it whilst nitrogen is passed over it.

It should be appreciated that a composition to be treated may be contacted with the adsorbent more than once. In such a process, the composition may be subjected to repeated contacts with one type of adsorbent or subjected to contacts with more than one type of adsorbent. Repeated contact will further reduce the content of the one or more undesired sulphur containing impurities and, if appropriate, of the one or more undesired halogenated organic compounds.

Typically, the composition to be treated may be contacted with the adsorbent as many times as necessary to remove the malodour and/or so that no sulphur containing impurities are detected using gas chromatography with pulsed flame detection set to sulphur mode. The number of times that a composition is contacted with the adsorbent depends on a number of factors, such as the freshness of the adsorbent and the initial level of impurities.

Typically, it is not necessary to subject the (hydro)halocarbon composition to any additional treatment(s) prior to or after the process of the present invention in order to ensure that there is no malodour.

However, if desired, the process can include one or more additional purifying steps, which may be conducted before and/or after the process of the present invention. The additional purifying steps may reduce the concentration of undesired sulphur containing impurities that are reduced/removed by the adsorbent.

If the composition to be treated includes undesired halogenated organic compounds, additional purifying steps may be used to reduce the concentration of those halogenated compounds whose concentration is reduced by the adsorbent comprising an acid stable molecular sieve having a pore size of from 2 to 10 Å and/or an activated carbon and/or of other halogenated compounds.

The additional purifying steps may, optionally, reduce the concentration of other undesired compounds, such as water.

Any methods of purifying (hydro)halocarbons known in the art may be used as additional purifying steps. For example, treatment with molecular sieves that are not acid stable molecular sieves having a pore size of from 2 to 10 Å and/or with drying agents and/or distillation may be used.

Layers of different adsorbents and/or drying agents can be combined within a single polishing bed. The order of the layers can be selected by a person skilled in the art so as to provide the most efficient treatment.

If required, distillation can be conducted before and/or after the composition to be treated is contacted with the adsorbent(s) and/or drying agent(s) in the polishing bed.

According to another aspect of the invention, there is provided the use of an adsorbent comprising an acid stable molecular sieve having a pore size of from 2 to 10 Å and/or an activated carbon to reduce the concentration of at least one undesired sulphur containing impurity in a (hydro)halocarbon composition, such as those defined above.

This use may reduce the concentration of at least one undesired halogenated organic compound in a (hydro)halocarbon composition.

According to yet another aspect of the present invention, there is provided a composition that is substantially free of undesired sulphur containing impurities obtainable by a process as described above.

Preferably, the composition is 1,1,1,2-tetrafluoroethane (R-134a), 1,1,1,2,3,3,3-heptafluoropropane (R-227ea), 1,1,1,3,3-pentafluoropropane (R-245fa), 1,1,2,2,3-pentafluoropropane (R-245ca) or mixtures thereof that is substantially free of undesired sulphur containing impurities.

By the phrase "substantially free of undesired sulphur containing impurities", we mean that the undesired sulphur containing impurities are present in an amount that is less than that which results in a malodour detectable by smell and/or below the amount detectable by gas chromatography. The skilled person will appreciate that the exact amount of undesired sulphur containing impurities will depend on which sulphur containing impurities were present in the composition before the process is conducted because different compounds have different malodour threshold and may be detectable at different levels using gas chromatography.

Compositions obtainable by a process as described above may be used as a propellant, especially as a pharmaceutical propellant. Halogenated alkanes, such as hydrofluoroalkanes, for example 1,1,1,2-tetrafluoroethane (R-134a), 1,1,1,2,3,3,3-heptafluoropropane (R-227ea), 1,1,1,3,3-pentafluoropropane (R-245fa), 1,1,2,2,3-pentafluoropropane (R-245ca) and mixtures thereof are suitable for this use.

Compositions obtainable by a process as described above may also be used as a refrigerant, as a foam blowing agent, as a solvent and/or as a fire extinguishing agent.

For example, 1,1,1,2-tetrafluoroethane (R-134a) obtainable by a process as described above may be used as a solvent, for example as an extraction solvent for natural products, preferably as a flavour and/or fragrance extraction solvent.

Figure 2:
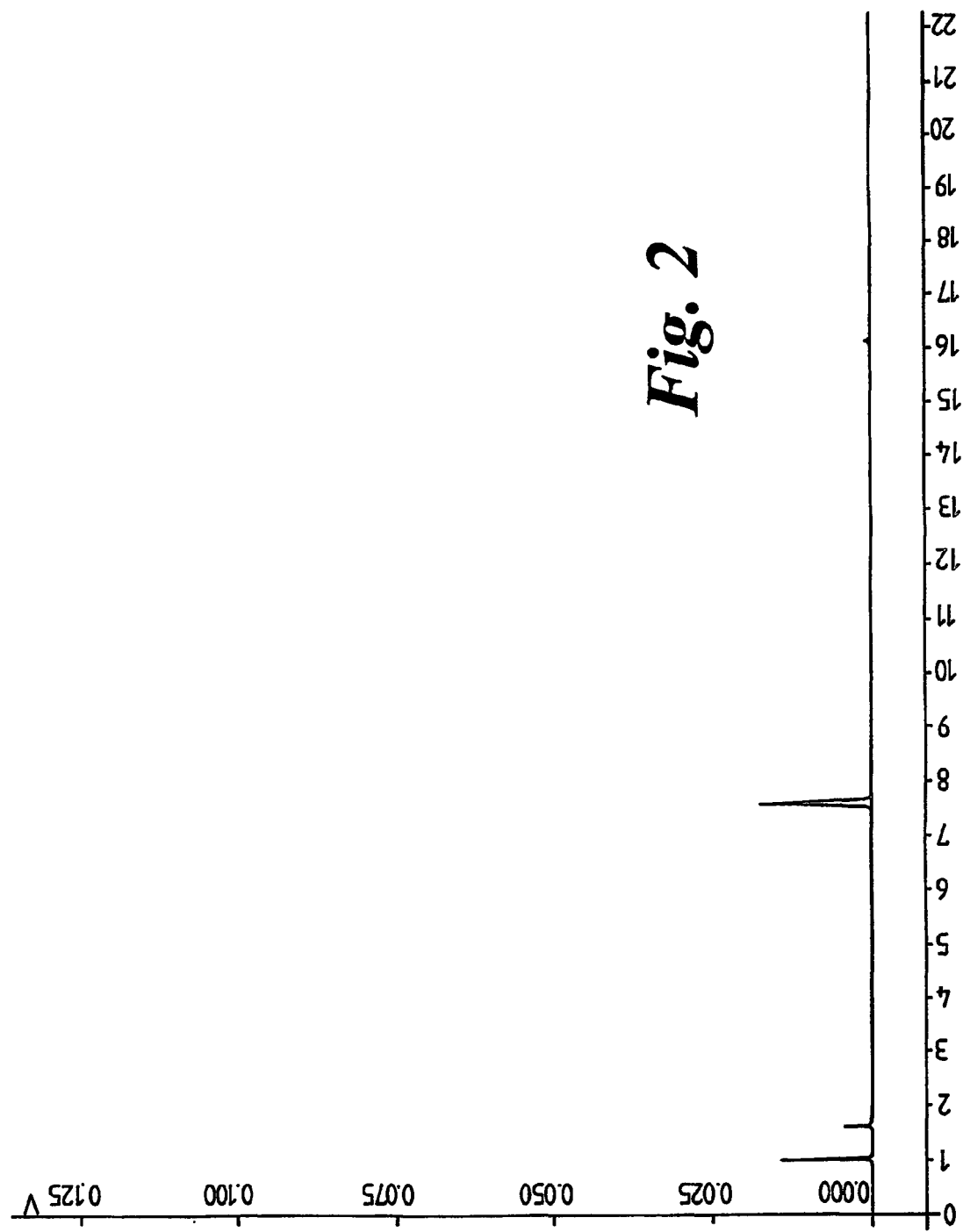
Figure 3:
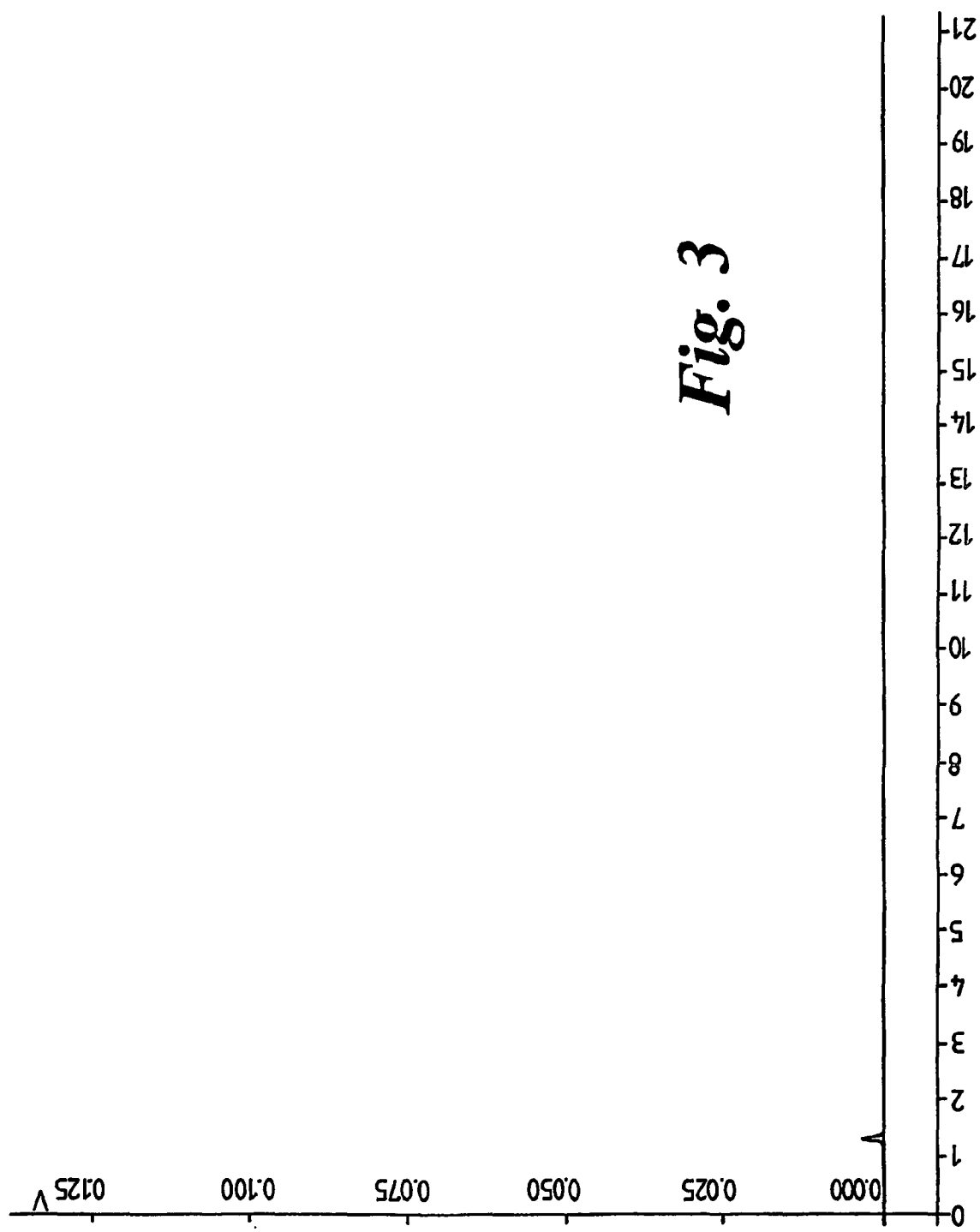

The present invention is now illustrated but not limited by the following Examples and FIGS. 1 to 3.

FIGS. 1 to 5 are gas chromatograms generated using a Varian 3800 gas chromatogram with pulsed flame photometric detection set to "sulphur" mode. The Figures relate to Examples 1 and 3.

EXAMPLE 1

This Example was conducted to show how effective each of the molecular sieves 4A and AW-300 are at reducing the levels of organic sulphur containing impurities present in R-134a.

R-134a was contacted with each of the molecular sieves for a period of twenty four hours at ambient temperature by placing both the R-134a and the molecular sieve in a container in the following amounts:

(a) 350 g of R-134a and 42 g of molecular sieve 4A.
(b) 500 g R-134a and 10 g of molecular sieve AW-300.

FIGS. 1 to 3 are gas chromatograms generated using a Varian 3800 gas chromatogram with pulsed flame photometric detection set to "sulphur" mode. Thus, the gas chromatograms show the organic sulphur containing impurities present in the R-134a.

FIG. 1 shows the gas chromatogram of the R-134a before contact with the molecular sieve. FIG. 2 shows the gas chromatogram of the R-134a after contact with molecular sieve (a) and FIG. 3 shows the gas chromatogram of the R-134a after contact with molecular sieve (b).

A comparison of FIGS. 2 and 3 shows a relatively poor removal of organic sulphur containing impurities using molecular sieve (a) compared to molecular sieve (b).

EXAMPLE 2

22 tonnes of liquefied R-134a were circulated through a reaction vessel containing 0.5 tonnes of molecular sieve AW-300 at a rate if 2.5 tonnes per hour for a total period of 18 hours at ambient temperature.

Examples of how the process of the present invention typically reduces the concentration of particular undesired halogenated impurities in (hydro)halocarbons are as follows:

| Undesired halogenated Impurity | Level before the process is conducted (ppm) | Level after the process is conducted (ppm) |
| --- | --- | --- |
| R-1131 | 0.5 | <0.1 |
| R-1122 | 4 | 0.7 |
| cis-R-1122a | 1 | <0.1 |
| R-22 | 2 | <0.1 |
| R-134 | 300 | 270 |
| R-31 | 5 | <0.1 |
| R-152a | 1 | 0.5 |

After treatment, levels of sulphur containing impurities were found to be below the limit of detection, as determined by smell.

EXAMPLE 3

300 g R-134a was contacted with 25 g of activated carbon (grade 207C purchased from Sutcliffe Speakman Carbons Limited), for a period of twenty four hours at ambient temperature by placing both the R-134a and the activated carbon in a container. Activated carbon grade 207C is a high activity carbon in which greater than 60% of the pore size distribution proportion falls within the 2 to 20 Å range.

Figure 4:
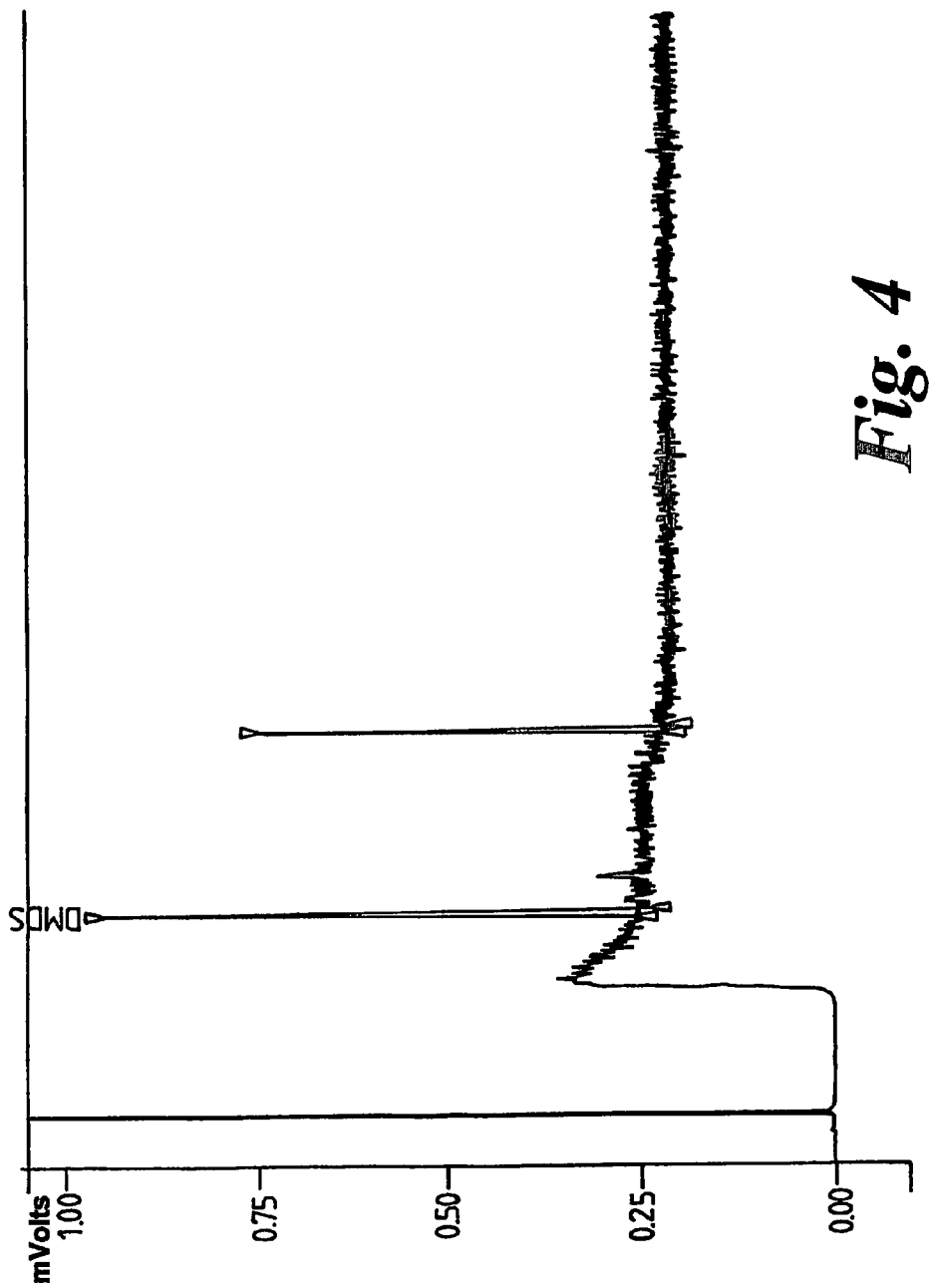
Figure 5:
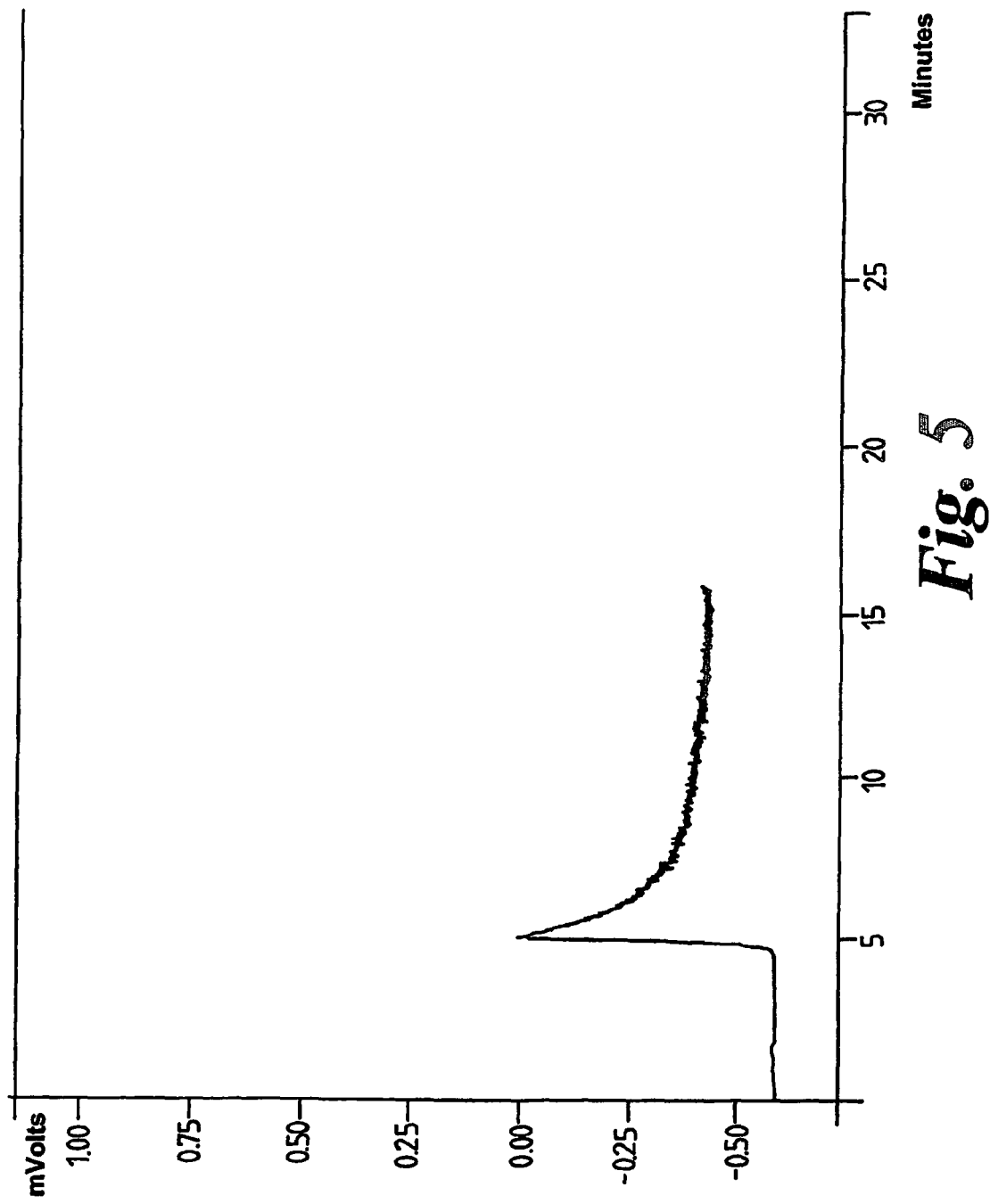

FIGS. 4 and 5 are gas chromatograms generated using a Varian 3800 gas chromatogram with pulsed flame photometric detection set to "sulphur" mode. Thus, the gas chromatograms show the organic sulphur containing impurities present in the R-134a.

FIG. 4 shows the gas chromatogram of the R-134a before contact with the activated carbon. FIG. 5 shows the gas chromatogram of the R-134a after contact with the activated carbon. FIG. 5 shows that all of the organic sulphur containing impurities (at least within the detection limit by gas chromatography) were removed from the R-134a following contact with the activated carbon.

The invention claimed is:

1. A process for reducing the concentration of at least one undesired sulfur containing impurity in a composition to be treated which comprises one or more desired (hydro)halocarbons and one or more of said undesired sulphur containing impurities, said process consisting of contacting said composition with an adsorbent comprising an acid stable molecular sieve having a pore size of from 2 to 10 Å and/or an activated carbon to reduce said concentration of said at least one undesired sulfur containing impurity.

2. A process as claimed in claim 1, wherein the composition to be treated also comprises one or more undesired halogenated organic compounds and said contacting with said adsorbent also reduces the concentration of at least one said undesired halogenated organic compound.

3. A process as claimed in claim 1, wherein the composition to be treated comprises at least one desired (hydro)halocarbon having a carbon chain length of from one to four.

4. A process as claimed in claim 1, wherein the composition to be treated comprises at least one desired (hydro)halocarbon selected from halogenated alkanes, halogenated alkenes and halogenated ethers.

5. A process as claimed in claim 3, wherein the composition to be treated comprises at least one desired (hydro)halocarbon selected from hydrofluoroalkanes, hydrochlorofluoroalkanes, chlorofluoroalkanes, perfluoroalkanes, perchloroalkenes, hydrochloroalkenes and (hydro)fluoroethers.

6. A process as claimed in claim 5, wherein the hydrofluoroalkane is at least one of 1,1,1,2-tetrafluoroethane (R-134a), 1,1,1,2,3,3,3-heptafluoropropane (R-227ea), 1,1-difluoroethane (R-152a), 1,1,1-trifluoroethane (R-143a), pentafluoroethane (R-125), difluoromethane (R-32), 1,1,1,3,3-pentafluoropropane (R-245fa), 1,1,2,2,3-pentafluoropropane (R-245ca), 1,1,1,3,3-pentafluorobutane (R-365mfc) and hexafluorobutane (R-356).

7. A process as claimed in claim 5, wherein the hydrochlorofluoroalkane is at least one of chlorodifluoromethane (R-22), 1,1-dichloro-1-fluoroethane (R-141b), 1-chloro-1,1-difluoro ethane (R-142b), 1,1,1-trifluoro-2-chloroethane (R-133a), 2,2-dichloro-1,1,1-trifluoroethane (R-123), 2-chloro-1,1,1,2-tetrafluoroethane (R-124) and dichloropentafluoropropane (R-225).

8. A process as claimed in claim 5, wherein the chlorofluoroalkane is at least one of dichlorodifluoromethane (R-12), 1,2-dichloro-1,1,2,2-tetrafluoroethane (R-114) and 1,1,1-trichloro-2,2,2-trifluoroethane (R-113a).

9. A process as claimed in claim 5, wherein the perfluoroalkane is at least one of perfluoromethane (R-14), perfluoroethane (R-116), perfluoropropane (R-218), perfluorobutane, perfluorocyclobutane, perfluoropentane and perfluorohexane.

10. A process as claimed in claim 5, wherein the perchloroalkene is perchloroethene.

11. A process as claimed in claim 5, wherein the hydrochloroalkene is at least one of trichloroethene and vinyl chloride.

12. A process as claimed in claim 5, wherein the hydrofluoroether is at least one of 1,1,1,3,3,3-hexafluoroisopropyl fluoromethyl ether, 1,1,1-trifluoro-2-chloroethyl difluoromethyl ether, 1,1,1,2-tetrafluoroethyl difluoromethyl ether, trifluoromethyl difluoromethyl ether and 1,1,1-trifluoroethyl tetrafluoroethyl ether.

13. A process as claimed in claim 1, wherein said at least one undesired sulphur containing impurity includes one of hydrogen sulphide, carbon disulphide, carbonyl sulphide, sulphur dioxide, sulphur trioxide, sulphuric acid, dimethyldisulphide, ethanethiol and diethyldisulphide.

14. A process as claimed in claim 2, wherein said one or more undesired halogenated organic compounds include at least one of chlorofluoromethanes, difluoroethanes, tetrafluoroethanes, chlorodifluoroethenes and chlorofluoroethenes.

15. A process as claimed in claim 1, wherein the adsorbent comprises an acid stable molecular sieve having a pore size of from 3 to 5 Å.

16. A process as claimed in claim 15, wherein the adsorbent comprises an acid stable molecular sieve having a pore size of from 3 to 4 Å.

17. A process as claimed in claim 1, wherein the adsorbent comprises a zeolite.

18. A process as claimed in claim 17, wherein the adsorbent comprises AW-300 molecular sieve.

19. A process as claimed in claim 1, wherein the adsorbent comprises an activated carbon.

20. A process as claimed in claim 1, which is conducted in the liquid phase.

21. A process as claimed in claim 1, which is conducted at a temperature of less than 100° C.

22. A process as claimed in claim 1, further comprising regenerating the adsorbent after it has been removed from the (hydro)halocarbon composition.

23. A process as claimed in claim 1, wherein said contacting with said adsorbent reduces said concentration of said undesired sulfur containing impurities by at least 50% by weight.

24. A process as claimed in claim 1, wherein said contacting with said adsorbent reduces said concentration of said undesired sulfur containing impurities by at least 90% by weight.

25. A process as claimed in claim 1, wherein said contacting with said adsorbent reduces said concentration of said undesired sulfur containing impurities by at least 98% by weight.

26. A process as claimed in claim 1, wherein said contacting with said adsorbent reduces said concentration of said undesired sulfur containing impurities to a level below the limit of detection.

27. A process as claimed in claim 1, wherein said contacting with said adsorbent reduces said concentration of said undesired sulfur containing impurities to a level below the limit of detection by smell and/or chromatography.

* * * * *